United States Patent [19]

Pilz

[11] Patent Number: 6,146,896
[45] Date of Patent: Nov. 14, 2000

[54] METHOD AND APPARATUS FOR MEASURING THE NITRIFICATION EFFECTIVENESS OF ACTIVATED SLUDGE

[75] Inventor: Ulrich Pilz, Berlin, Germany

[73] Assignee: LAR Analytik und Umweltmesstechnik GmbH, Berlin, Germany

[21] Appl. No.: 08/934,195

[22] Filed: Sep. 19, 1997

[30] Foreign Application Priority Data

Sep. 19, 1996 [DE] Germany ............................ 196 40 333

[51] Int. Cl.[7] ................................................... G01N 33/18
[52] U.S. Cl. ........................... 436/62; 436/106; 436/110; 436/127; 436/138; 436/181; 422/79; 422/80; 435/29; 435/287.1; 210/601; 210/611; 210/612; 210/613; 210/614
[58] Field of Search ............................. 436/52, 62, 106, 436/110, 111, 127, 138, 139, 175, 181; 422/68.1, 79, 80; 435/29, 34, 287.1; 210/601, 610, 611, 612, 613, 614

[56] References Cited

U.S. PATENT DOCUMENTS

| | | | |
|---|---|---|---|
| 4,329,232 | 5/1982 | McKenna | 210/614 |
| 4,620,930 | 11/1986 | McDowell | 210/614 |
| 4,693,827 | 9/1987 | Mordorski | 210/614 |
| 4,898,829 | 2/1990 | Siepmann et al. | 435/286.5 |

FOREIGN PATENT DOCUMENTS

| | | |
|---|---|---|
| 2951707 | 7/1981 | Germany . |
| 3932640 | 4/1991 | Germany . |

(List continued on next page.)

OTHER PUBLICATIONS

Surmacz–Gorska et al. *Water Research,* vol. 30, No. 5, pp. 1228–1236, 1996.

(List continued on next page.)

*Primary Examiner*—Maureen M. Wallenhorst
*Attorney, Agent, or Firm*—Venable; George H. Spencer; Ashley J. Wells

[57] ABSTRACT

A method and apparatus for determining nitrification effectiveness of activated sludge in an aqueous solution, includes supplying equivalent quantities of an activated sludge, an aqueous solution, and a gas containing oxygen to each of first and second reaction vessels; simultaneously delivering a nitrification inhibitor to only the second reaction vessel; performing a bacterial respiration reaction in the vessels for either a preselected period of time or continuously in which case the materials are supplied per unit of time so that the bacterial respiration reaction in the first reaction vessel, where oxygen consumption as a result of total bacterial respiration occurs and includes oxygen consumption as a result of endogenous respiration, oxygen consumption as a result of nitrification, and oxygen consumption as a result of degradation of carbon compounds, may be compared with the respiration reaction in the second reaction vessel where oxygen consumption includes oxygen consumption as a result of endogenous respiration, and oxygen consumption as a result of degradation of carbon compounds, but where oxygen consumption as a result of nitrification is at least inhibited; measuring oxygen content for each of the vessels after the same reaction time either above the respective aqueous solutions or continuously in respective waste gas streams escaping from the respective reaction vessels to obtain at least one measured value for the respective vessels of one of oxygen content or a variable derived therefrom; determining the nitrification effectiveness of the activated sludge per unit quantity thereof by subtracting the measured values for the second reaction vessel from the first reaction vessel to provide a difference value; supplying the equivalent preselected quantities of an activated sludge including nitrifying bacteria, pure water, and a gas containing oxygen to a third reaction vessel; and performing a bacterial respiration reaction in the third reaction vessel for either the predetermined period of time or continuously so that the bacterial respiration reaction in the third reaction vessel where oxygen consumption is due only to endogenous respiration may be compared to that in at least one of the first and second reaction vessels.

18 Claims, 3 Drawing Sheets

FOREIGN PATENT DOCUMENTS

| | | |
|---|---|---|
| 4130465 | 3/1993 | Germany . |
| 03032799 | 2/1991 | Japan . |
| 4122498 | 4/1992 | Japan . |
| 5192688 | 8/1993 | Japan . |
| 5228485 | 9/1993 | Japan . |
| 6312197 | 11/1994 | Japan . |
| 8117792 | 5/1996 | Japan . |

OTHER PUBLICATIONS

Robinson. *Toxicity Assessment : An International Journal,* vol. 3, pp. 17–31, 1988.

Chemical Abstracts 85 (1976) 181947n; Stensel, H.D.etal. J. Water Pollut. Control Fed. 48 (1976) 2343–2350.

METHOD AND APPARATUS FOR MEASURING THE NITRIFICATION EFFECTIVENESS OF ACTIVATED SLUDGE

BACKGROUND OF THE INVENTION

1. Field of the Invention

The invention relates to a method for determining the nitrification effectiveness of activated sludge in an aqueous solution (especially water to be purified, or wastewater) and to an apparatus for performing the method.

2. Description of the Related Art

Analysis of water or wastewater for its ingredients and the adjuvants added in the purification/disposal, with regard to their specific effectiveness, is an unavoidable prerequisite to efficient water purification and wastewater disposal in view of the high quality currently demanded.

In the clarification of wastewater from both private and commercial sources, the (biological) degradation of organic hydrocarbon compounds is an urgent goal. In combination with biological purification, the content of biodegradable substances, as expressed in the biological oxygen demand, is a variable of the same decisive importance as the metabolism of the aerobic bacteria that are essential for the purification.

From German Patent DE 29 51 707 C2, a device for determining the concentration of biodegradable substances in wastewater is known, with which the biological oxygen demand of the wastewater (as a measure for this concentration) is ascertained by way of a comparative measurement of the difference in oxygen concentration at the inlet and outlet of two parallel-operated reactors.

As a consequence of the degradation of the hydrocarbon compounds, especially as a byproduct of bacterial digestion of proteins, nitrogen compounds form (ammonium), which disadvantageously cause eutrofication of groundwater and represent a danger to the fish population. These byproducts must therefore also be eliminated in the course of the wastewater purification. The elimination of the ammonium proceeds in two stages: First, by special microorganisms ("nitrifying bacteria") that breathe oxygen dissolved in the water, ammonium is oxidized ("aerobically") into nitrite and nitrate, and then by other microorganisms (denitrification) under oxygen deficiency conditions, the nitrate is reduced (quasi-"anaerobically") into gaseous nitrogen, which can escape into the atmosphere without being processed further.

The bacteria (nitrifying bacteria)—of the genera Nitrobacter and Nitrosomonas—make difficult demands in terms of nutrients, temperature, pH, and other ambient conditions and in particular are very vulnerable to pollutants. Their effectiveness, which determines the nitrification effectiveness of an activated sludge, must therefore be monitored as continuously as possible, for the sake of closely timed control of the purification process as a function of this important variable, and in particular for the sake of optimizing the factors that are involved in the nitrification effectiveness itself. As a result, there is a need for a method and an apparatus for performing it, with which the metabolism of these bacteria and the nitrification effectiveness determined thereby of an activated sludge can be detected continuously by measuring instruments.

The object of the invention is to disclose such a method and a corresponding apparatus.

SUMMARY OF THE INVENTION

In terms of the method, this object is attained by a method for determining nitrification effectiveness of activated sludge in an aqueous solution, in particular water laden with hydrocarbons, having the following steps: supplying a predetermined or measured quantity of activated sludge, of aqueous solution and of air or oxygen to a first and the second reaction vessel, simultaneous delivery of a nitrification inhibitor to only the second reaction vessel; performing a respiration reaction in the first and second reaction vessels for a predetermined period of time or continuously, with a predetermined quantity of activated sludge, aqueous solution, and air or oxygen per unit of time; measuring the oxygen content above the aqueous solution in the first and second reaction vessel after the same reaction time in both reaction vessels, or continuously in a waste air stream escaping from the respective reaction vessel; and comparatively evaluating the measured oxygen content values ascertained at the first and second reaction vessels, taking into account quantities of starting materials and forming a difference between the measured oxygen content values or the values of a variable derived from them. In terms of the apparatus, this object is attained by an apparatus for performing the inventive method, characterized by at least one first and second reaction vessel, to each of which delivery devices are assigned for delivering aqueous solution, activated sludge and air or oxygen, only one of the reaction vessels additionally being assigned a device for delivering a nitrification inhibitor, means for predetermining or measuring the supplied quantities of aqueous solution, activated sludge and air or oxygen, at least one first and second oxygen sensor, assigned to the first reaction vessel, for measuring the oxygen content above the aqueous solution in the first and second reaction vessels, or in a waste air stream from them, and an evaluation device, connected to the predetermining or measuring means and to the sensors, for ascertaining the standardized nitrification-oxygen reaction, which has a subtraction unit for forming the difference between the output signals of the first and second oxygen sensors or between signals derived from them.

The invention encompasses the idea that to determine the nitrification effectiveness, it is suitable to determine the oxygen reaction associated with this process, that is, an oxygen mass balance. It also includes the idea that to determine this oxygen reaction, a comparative oxygen content measurement at the inlet and outlet of a biological reactor containing the activated sludge to be tested can be employed, if it is possible to correct the outcome of measurement—which reflects the total bacterial respiration—by various components that do not express the oxygen consumption as a consequence of the nitrification but instead express other processes in the reactor. Such processes are on the one hand so-called endogenous respiration of the bacteria, that is, the maintenance of their pure living functions (without the degradation of carbon compounds or ammonium), and on the other the aforementioned degradation of the carbon compounds.

In the final analysis, these thoughts lead to the teaching which forms the nucleus of the present invention, that is, to ascertain the nitrification oxygen reaction on the basis of a comparative determination of the oxygen reaction in two reactors, with nitrification occurring in one of the reactors while being prevented in the other; this makes it possible to separate the various respiration components.

In an advantageous refinement of the concept of the invention, a still more extensive separation is done in order additionally to determine the so-called biochemical oxygen demands (BSB in German, or "BOD" for the term in English, "biochemical oxygen demand"), by using a third reactor which instead of being filled with wastewater or contaminated water is filled with pure water and in which the activated sludge can therefore perform only an endogenous respiration. The BOD is ascertained from the difference in the oxygen reaction in the reactor in which a reaction of the carbon compounds in the wastewater occurs but nitrification is inhibited, and in the latter reactor in which only endogenous respiration occurs.

Another possible way of additionally determining the BOD is presented if the oxygen reaction as a consequence of endogenous respiration can be considered to be known at the outset: Then the third reactor can be dispensed with, and the BOD can be ascertained on the basis of a corrective calculation from the oxygen reaction in the second reactor (with inhibited nitrification).

Additional possible ways of determining the organic water or wastewater ingredients are offered by a further modification of the method, in which at least one of the first and second reaction vessels, in addition the carbon dioxide content is measured above the aqueous solution or continuously in the waste air stream, and a carbon balance is obtained therefrom. From this—naturally again on the basis of the known quantities or volumes of the starting materials—a carbon balance can be obtained.

In the event that the oxygen content of the gas mixture supplied to the reaction vessels—which in air is about 20%—is not known, or is not known sufficiently precisely, the oxygen content is also measured at the inlet to the reaction vessels, and the evaluation is made on the basis of the difference between the oxygen content on the inlet side and that on the outlet side.

One of the major practical advantages of the method of the invention is in particular that it can be performed continuously, and the quantities of starting materials—strictly speaking, with the exception of the nitrification inhibitor, whose quantity plays no role as long as it suffices to reliably inhibit the nitrification reaction— supplied to the reaction vessels per unit of time are advantageously determined via means for controlling the flow (such as metering pumps), or via flow rate measurement.

The calculations, which are intended as much as possible to furnish closely timed results, are simplified and thus shortened in terms of time if, expediently, the first and second reaction vessels, and the third reaction vessel—if provided—as well, are embodied identically from the standpoint of process technology.

This also includes establishing the most identical possible starting or flow quantities of the starting materials.

A proven active ingredient that can be used in the present method as a nitrification inhibitor is allylthiourea (abbreviated ATH in German).

If the water or wastewater to be purified is especially low in organic substance or ammonium, then the nutrient content for the nitrifying bacteria can act in a limiting manner on the nitrification effectiveness, which would make the finding with regard to the nitrification effectiveness dictated by the activated sludge metabolism incorrect. In that case, it may become necessary to add additional nutrients—sources of organic carbon (peptones, sugar, organic acids, etc.) or of nitrogen (ammonium or urea)—by metered addition of them to the first and second reactor courses.

Since nitrification is a temperature-sensitive process, it is important, if accurate and replicable results are to be obtained that the measuring method proceed at a substantially constant temperature that is the same for the reaction vessels. Preferably it is carried out in a range between 20° C. and 40° C. and even more particularly between 30° C. and 35° C.

In an advantageous refinement, a third reaction vessel, to which delivery devices for supplying pure water, activated sludge and air or oxygen are assigned, and a third oxygen sensor assigned to the third reaction vessel are provided in the apparatus for performing the method. In that case, the evaluation device is additionally embodied for ascertaining the biochemical oxygen demand and has a subtraction unit for forming the difference between the output signals of the second and third oxygen sensors or between signals derived from them. As in the apparatus specified in the main apparatus claim, the evaluation device is preferably embodied as a microcomputer or PC.

The reaction vessels are expediently systems with a continuous flow through them, with a so-called "plug-flow" or piston flow characteristic—such as tubular reactors or a series of agitator reactors connected one after the other—in which only slight longitudinal mixing of the liquid and air mixture takes place. Preferably, they have the same construction and the same dimensions.

In the version of the apparatus that also makes it possible to produce a carbon balance, a carbon dioxide sensor is assigned to at least one of the first and second reaction vessels, and the evaluation device communicates with it and is embodied to determine the carbon balance. Once again, this is achieved by software in a PC configuration.

In operation in a water or wastewater purification or clarification plant, the apparatus is expediently connected on the inlet side of the first and second reaction vessels directly to a water or wastewater line via a sampling tubule.

The reaction vessels are accommodated, preferably in common, in a thermostat, whose temperature is controllable in particular in the aforementioned temperature range.

In the version suitable for automatic operation, the apparatus has a sequence control unit which in particular controls the delivery of starting materials and the operation of the evaluation device and selectively also controls the process temperature.

The apparatus is advantageously employed in a water supply or wastewater disposal system, in order to control the system on the basis of the evaluation results obtained. The evaluation device then has a comparison value memory and a comparator unit for performing set-point and actual comparisons, or comparisons of current values with past values. Its output in that case is connected to the control unit of the process controller of that system, which is embodied to output control signals to final control elements, especially slide or metering agent adjusters, in the water supply or wastewater disposal plant.

BRIEF DESCRIPTION OF THE DRAWINGS

Other advantageous refinements of the invention are defined by the dependent claims and will be described in further detail below along with the description of the preferred embodiment of the invention, in conjunction with the drawings. Shown are:

DESCRIPTION OF THE PREFERRED EMBODIMENTS

Figure 1:
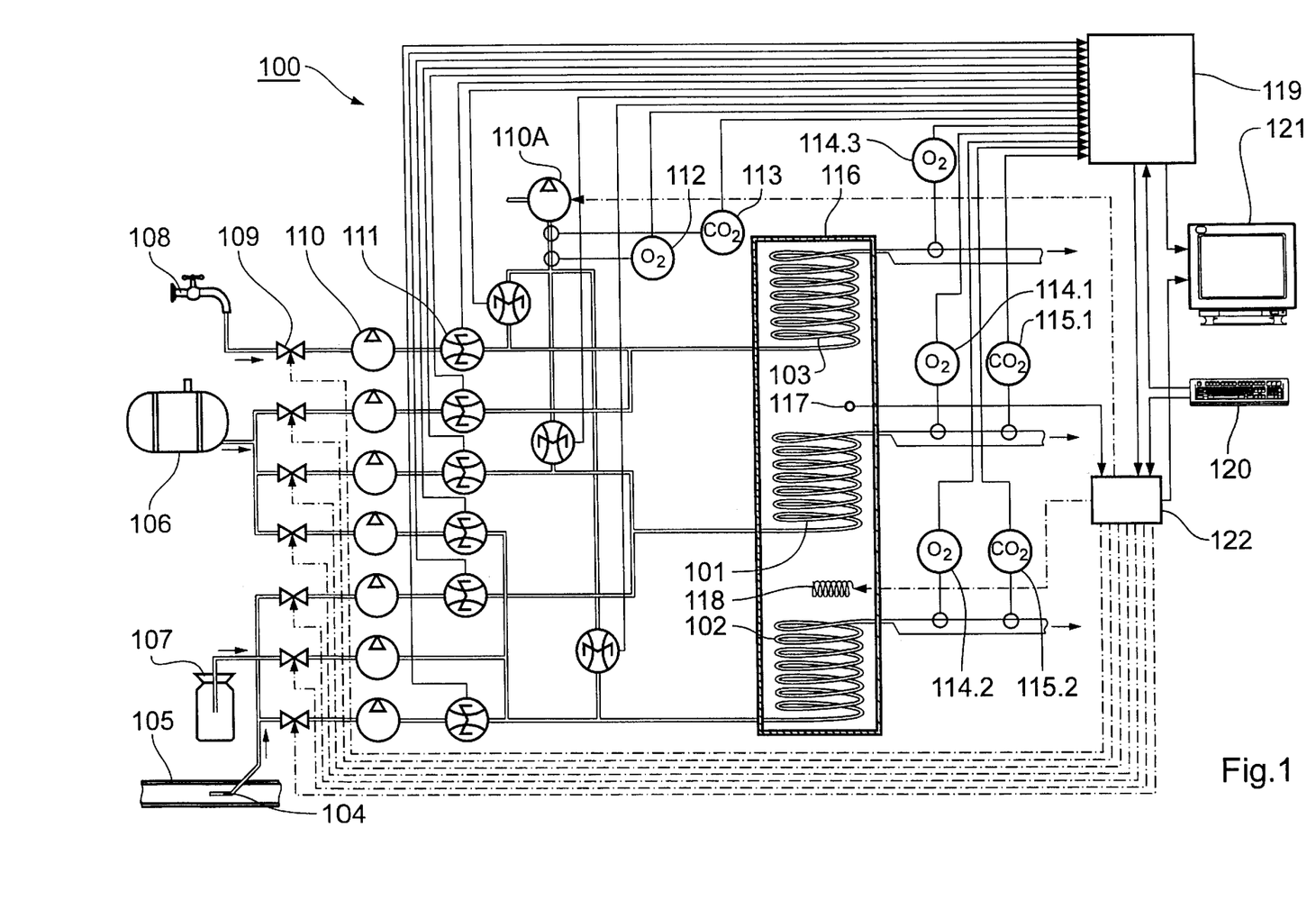
FIG. 1, an apparatus for performing the method of the invention in a first embodiment.

FIG. 1 shows a measurement apparatus 100 for determining the nitrification effectiveness of the activated sludge in a clarification plant and for determining the biochemical oxygen demand and the carbon balance of wastewater; it has three tubular reactors 101, 102 and 103 of identical structure and identical dimensions. The first tubular reactor 101 communicates on the inlet side with a sampling tubule 104, which protrudes into a tube 105 leading into the wastewater to be examined. Its inlet also communicates with a source (shown here symbolically as a tank 106) for the activated sludge. The second tubular reactor 102 likewise communicates on its inlet side with the sampling tubule 104 and the activated sludge tank 106 and also communicates with a container 107 that contains allylthiourea as a nitrification inhibitor. The third tubular reactor 103, finally, likewise communicates with the activated sludge tank 106, but not with the sampling tubule, and instead communicates with a freshwater supply inlet 108. All three reactors have an incoming air line, by way of which the compressed air is fed into the inlet of the reactors. On the outlet side, all the reactors—although this is not shown in the drawing—discharge into the wastewater pipe 105 (downstream of the sampling tubule 104) or directly into the clarification plant.

On the inlet side, in each line branch, one shutoff valve 109 and one feed pump 110 and—with the exception of the line communicating with the container 107—one flow rate meter 111 are provided. (For the sake of simplicity in the drawing, these components are not identified by separate reference numerals but instead are merely identified once in the uppermost line between the freshwater supply inlet 108 and the third reactor 103.) The incoming air lines communicate with one common air pump 110A, which aspirates from the atmosphere.

Also disposed in the incoming air line are an inletside fuel cell 112 and an inlet-side $CO_2$ sensor 113, and on the outlet side of all the reactors (in the gas space above the liquid stream), there are a respective outlet-side fuel cell 114.1–114.3 and, for the first and second reactors, an outlet-side $CO_2$ sensor 115.1 and 115.2, which detect the oxygen and $CO_2$ content in the incoming air or in the exhaust gas stream from the reactors.

The reactors 101–103 are located in a heat-insulating housing 116, in which a temperature sensor 117 and a temperature adjuster 118—symbolically shown as a heating coil in the drawing—are also disposed.

All the flow rate meters, fuel cells and $CO_2$ sensors communicate with data inputs of an evaluation device 119, which on the input side is also connected to a control keyboard 120, as a command input unit, and on the output side to a screen 121 as a display unit and to a microcontroller 122. The evaluation device 119, in the arrangement shown here, is in turn connected on the input side to the temperature sensor 117 via a data line, and on the output side to the shutoff valves 109 and the temperature control device 118 via control lines. In practice, the components 119–122 may be embodied economically as a standard PC configuration, and evaluation and control software tailored to the method is employed.

The method procedure is as follows:

After the opening of the shutoff valves 109 and after the feed pumps 110 and 110A are put into operation, the starting materials, in the association specified by the line courses and in a quantity (per unit of time) specifically ascertained for each reactor and each starting material (except for the nitrification inhibitor) by the flow rate meter 111, are supplied to the reactors 101–103. The oxygen and $CO_2$ concentrations are detected continuously at the inflow line. At the outlets of all the reactors, via the various fuel cells, the oxygen concentration above the outflowing reaction product is detected continuously, and the $CO_2$ concentration is moreover detected at the outlets of the first and second reactor.

The allylthiourea is metered to the second reactor 102 in an amount that assures reliable inhibition of the nitrification reactions. In the first reactor 101, to which no allylthiourea is supplied, however, these reactions proceed—along with the reaction of the hydrocarbons, which takes place in both reactors—in the same way as in the clarification plant, which uses the same activated sludge as the measurement arrangement. The third reactor 103 is supplied with only pure water or nutrients, so that here only the endogenous respiration of the activated sludge microorganisms occurs. The drop in the oxygen content that can be found in this reactor—in the form of a difference between the $O_2$ measured values recorded by the sensors 112 and 114.3—reflects the consumption of oxygen as a consequence of endogenous respiration; the difference between the measured values of the oxygen sensors 112 and 114.2 in the second reactor reflects the oxygen consumption from endogenous respiration and respiration of the hydrocarbon compounds in the wastewater; and finally, the difference between the measured values of the sensors 112 and 114.1 in the first reactor reflects the oxygen consumption from endogenous respiration, reaction of the hydrocarbon compounds, and nitrification. The difference in the measured values of the $CO_2$ sensors 13 and 115.1 or 115.2, finally, makes possible a finding regarding the carbon balance of the reaction and thus allows additional conclusions to be drawn as to the organic ingredients in the wastewater.

Processing the measured values with the flow quantity values of the starting materials in the evaluation device, using a suitable algorithm (including the aforementioned formation of differential values) therefore furnishes ongoing current specific oxygen balances for the aforementioned processes, as well as a carbon balance, from which conclusions can be drawn, on the one hand as to the metabolism or current nitrification effectiveness of the activated sludge and on the other as to the current BOD and the organic ingredients in the wastewater. If model data and/or past data for calibration purposes are available, then the aforementioned important variables of the activated sludge or of the wastewater to be purified can be displayed directly on the screen. From the results of the evaluation, the process conditions of the measurement method can moreover be modified—via the controller 122—for instance in order to avoid limitations in the nitrification reaction that falsify the results caused by the quantity or composition of the starting materials, to maximize the sensitivity for one or the other measured variable. If necessary, from supply containers (not in the drawing), nutrients can additionally be supplied to the wastewater in controlled fashion. The current parameters of the measuring method can be shown on the screen 121, and via the keyboard the operator can intervene both into the course of the process and into the evaluation and display of the outcomes of the evaluation. The method parameters for the reactions in the first and second reactors are expediently made to approximate the conditions in the clarification plant as closely as possible—especially with regard to the proportional quantities of the starting materials and to the temperature.

Figure 2:
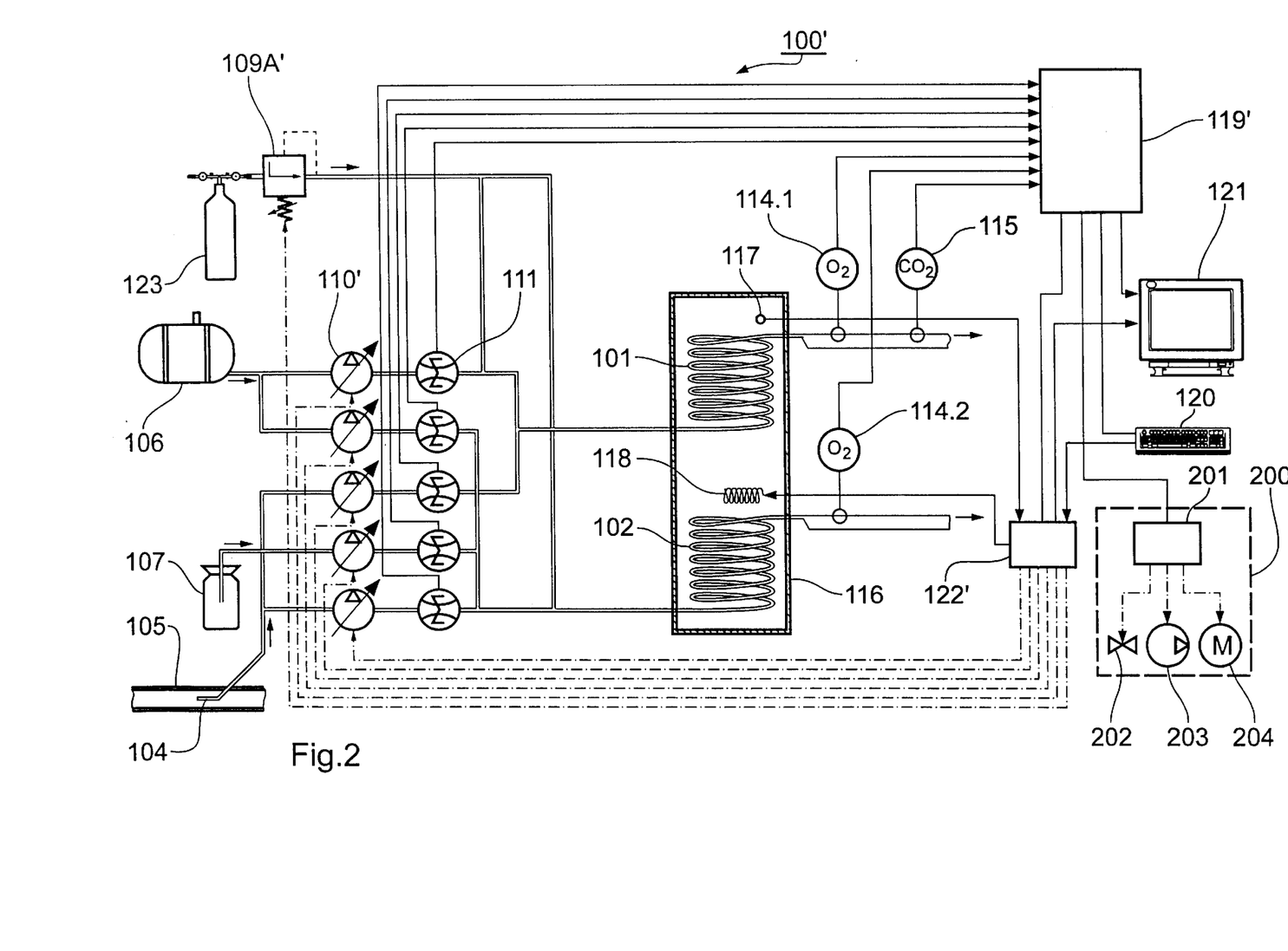
FIG. 2, an apparatus for performing the method of the invention in a second embodiment.

FIG. 2 shows a measurement arrangement 100' that is modified compared with the arrangement of FIG. 1. However, a majority of the components are equivalent to those shown in FIG. 1; they are identified by the same reference numerals as in that drawing and will not be described again below. One substantial difference is the elimination of the third reactor, and another is that the air supply from the atmosphere is replaced with a supply of oxygen from a pressurized cylinder 123 via a controllable metering valve 109A'. No shutoff valves are provided in this version, and the feed pumps are designed as metering pumps 110'. Since the oxygen content of the gas supplied is precisely known here (close to 100%, per specification by the supplier), and it does not contain $CO_2$, the inlet-side $O_2$ and $CO_2$ sensors are omitted.

For the evaluation—which makes it possible to eliminate the third reactor—the oxygen consumption from endogenous respiration of the activated sludge (bacterial respiration) is assumed to be known, so that the evaluation device 119' (which is naturally also modified in terms of the software used) is supplied along with the flow rate quantity values only with the measured values ascertained by the outlet-side $O_2$ sensors and by an outlet-side $CO_2$ sensor 115. The evaluation is done on the principle explained above and in principle leads to the same findings—with the exception that predetermined values are used instead of some measured values. The evaluation device 119' is connected additionally here to one input of a process control unit 201 of the clarification plant 200, so that from the evaluation results, direct intervention into the control of the clarification process can be obtained. This is symbolically represented in the drawing by showing the process control unit in turn connected to a shutoff valve 202, a feed pump 203, and a control motor 204. By actuating such control means, it is possible for instance as a function of the detected current nitrification effectiveness of the activated sludge, or of its development over time, to obtain a means for adjusting the pH value or to take provisions to eliminate the toxic substances that impair nitrification.

The measurement arrangement shown in FIG. 2 can be further simplified, for instance by eliminating the flow rate meters as well and by supplying the evaluation device instead with the control signals of the controller for the metering pumps directly. Under certain circumstances, active temperature regulation can also be dispensable, as long as it is merely assured that the reactors have essentially the same process temperature. The tubular reactors may be replaced with cascades—known per se—of agitator reactors (preferably, 3 or 4 such reactors). If findings only on nitrification effectiveness and on the BOD but not on a carbon balance are needed, then detecting and evaluating the $CO_2$ content can be dispensed with. With the two-reactor arrangement of FIG. 2, analysis is possible in principle even if the oxygen consumption from endogenous respiration is unknown. If the charging is done in the way shown in FIG. 2, then in this case the BOD cannot be ascertained separately, however. Still, it is possible for the oxygen demand for the bacterial respiration in the same system or plant to be determined by means of a separate calibrating measurement (preferably beforehand) and for the thus-determined value to be used—as at least an approximate value—for the ensuing continuous measurement process.

Figure 3:
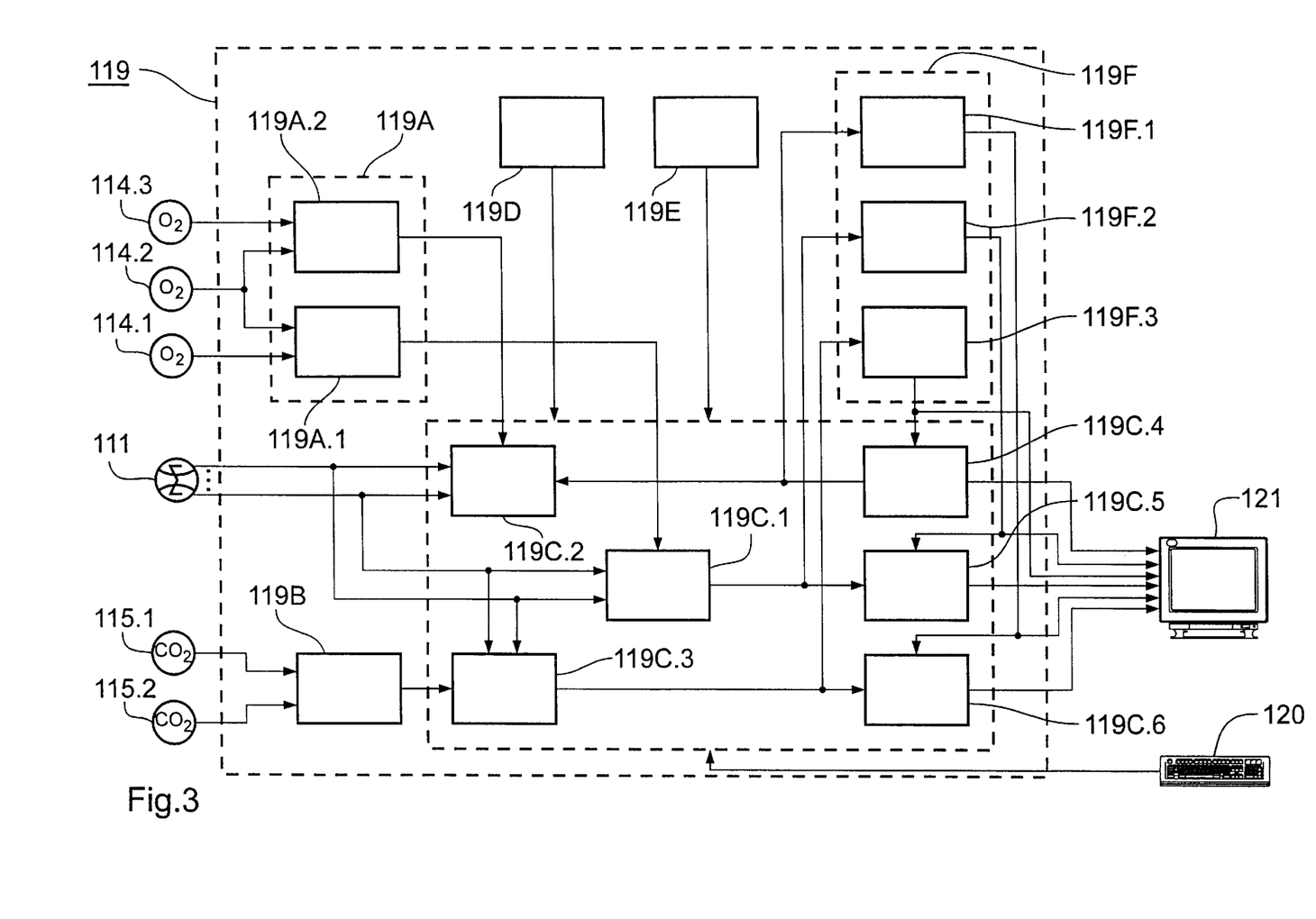
FIG. 3, a functional block circuit diagram as a detail of FIG. 1.

FIG. 3, in the form of a function block circuit diagram, shows essential functions or components of an evaluation device, taking the evaluation device 119 of FIG. 1 as an example.

This unit includes a subtraction stage 119A, connected to the $O_2$ sensors 114.1–114.2 and including two separate function units: a first subtraction unit 119A1, which is connected to the $O_2$ sensors 114.1 and 114.2 and forms the difference in the oxygen content values at the first and second reactor, and a second subtraction unit 199A.2, which is connected to the $O_2$ sensors 114.2 and 114.3 and forms the difference in the oxygen content values at the second and third reactors. It also includes a unit 119B, connected to the $CO_2$ sensors 115.1 and 115.2, for testing the plausibility of the measured $CO_2$ values.

The outputs of all the units named and the flow rate meter 111 all communicate with a processing unit 119C, to which—as usual—the input keyboard 120 and a program memory 119D and a working memory 119E are assigned. The processing unit 119C includes a first calculation stage 119C.1 for calculating the (standardized) current nitrification oxygen demand, a second calculation stage 119C.2 for calculating the standardized current BOD, and a third calculation stage 119C.3 for calculating the standardized current carbon balance. The outputs of these stages are connected to a respective FIFO memory 119F.1, 119F.2 and 119F.3 of a comparison value memory unit 119F, in each of which a progressively updated quantity of comparison values for the aforementioned variables is stored. The calculation stages are also each connected to one trend calculating unit 119C.4, 119C.5 and 119C.6, respectively, in which on the basis of the current values and the past values stored in the memories 119F.1–119F.3, trend analyses are performed, which make it possible to observe the wastewater composition in its course over time and to make conclusions about time-dependent processes in the clarification plant, especially in the activated sludge. At least some of the memorized values, and the results of the trend calculations, are shown on the screen 121 together with the current values of the relevant variables.

The invention is not limited in its embodiment to the preferred exemplary embodiments given above. On the contrary, there are many convceivable variants that make use of the basic version even in embodiments of different types.

What is claimed is:

1. A method for determining nitrification effectiveness of activated sludge in an aqueous solution, comprising the steps of:

supplying equivalent preselected quantities of an activated sludge including nitrifying bacteria, an aqueous solution, and a gas containing oxygen to each of first and second reaction vessels;

simultaneously delivering a nitrification inhibitor to only the second reaction vessel in an amount which is at least effective to inhibit nitrification of the aqueous solution;

performing a bacterial respiration reaction in the first and second reaction vessels for either a preselected period of time or continuously in which case the equivalent preselected quantities of activated sludge, aqueous solution, and gas containing oxygen are supplied per unit of time, so that the bacterial respiration reaction in the first reaction vessel, where oxygen consumption as a result of total bacterial respiration occurs and includes oxygen consumption as a result of endogenous respiration, oxygen consumption as a result of nitrification, and oxygen consumption as a result of degradation of carbon compounds, may be compared with the respiration reaction in the second reaction vessel where oxygen consumption includes oxygen consumption as a result of endogenous respiration, and oxygen consumption as a result of degradation of carbon compounds, but where oxygen consumption as a result of nitrification is at least inhibited;

measuring oxygen content for each of the first and second reaction vessels after the same reaction time either above the respective aqueous solutions or continuously in respective waste gas streams escaping from the respective reaction vessels to obtain at least one measured value for the first reaction vessel and for the second reaction vessel of one of oxygen content or a variable derived therefrom;

determining the nitrification effectiveness of the activated sludge per unit quantity thereof by subtracting one of the at least one measured value for the second reaction vessel from one of the at least one measured value for the first reaction vessel to provide a difference value;

supplying said equivalent preselected quantities of an activated sludge including nitrifying bacteria, pure water, and a gas containing oxygen to a third reaction vessel;

performing a bacterial respiration reaction in the third reaction vessel for either said preselected period of time or continuously in which case the equivalent preselected quantities of activated sludge, pure water, and gas containing oxygen are supplied per unit of time;

measuring oxygen content for the third reaction vessel either above the water in the third reaction vessel or continuously in a waste gas stream escaping from the third reaction vessel after a reaction time which is either the same as that for the first and second reaction vessels or continuously to obtain at least one measured value of one of oxygen content or a variable derived therefrom; and determining biochemical oxygen demand of the aqueous solution in the second reaction vessel by subtracting respective ones of the at least one measured value for the third reaction vessel from corresponding respective ones of the at least one measured value for the second reaction vessel.

2. The method of claim 1, further comprising:

determining a standard measured value for oxygen consumption which is due only to endogenous respiration in the activated sludge; and determining biochemical oxygen demand of the aqueous solution in the second reaction vessel by subtracting the standard measured value from the at least one measured value for the second reaction vessel.

3. The method of claim 1, further comprising:

measuring carbon dioxide content in at least one of the first and second reaction vessels either above the aqueous solution or continuously in the waste gas stream escaping therefrom to provide a plurality of carbon values; and determining a carbon balance from the plurality of carbon values by subtraction of two of the plurality of carbon values.

4. The method of claim 1, wherein each of the first and second reaction vessels has an inlet and an outlet, wherein the oxygen content of the gas containing oxygen is measured at the inlet and at the outlet of each of the first and second reaction vessels, and wherein oxygen consumption is determined by subtracting the oxygen content at the inlet side from that at the outlet side for the respective reaction vessels.

5. The method of claim 1, wherein the method is performed continuously, and wherein the preselected quantities of an activated sludge including nitrifying bacteria, an aqueous solution, and a gas containing oxygen supplied to each of the first and second reaction vessels per unit of time are determined by at least one of flow measurement and flow control.

6. The method of claim 1, wherein the first, second, and third reaction vessels are structurally identical and are operated with equivalent parameters including temperature, pH, and ambient conditions.

7. The method of claim 1, wherein the nitrification inhibitor is allylthiourea.

8. The method of claim 1, wherein an equivalent preselected quantity of a nutrient selected from the group consisting of an ammonium salt, a urea, a peptone, a sugar, and an organic acid is supplied to each of the first and second reaction vessels along with the aqueous solution.

9. The method of claim 1, wherein the method is performed at an essentially constant temperature which is the same for all the reaction vessels and which ranges from 20° C. to 40° C.

10. An apparatus for performing the method of claim 1, comprising:

first, second, and third reaction vessels;

delivery devices for delivering materials including an activated sludge including nitrifying bacteria, an aqueous solution, and a gas containing oxygen to each of the first and second reaction vessels;

delivery devices for delivering the activated sludge including nitrifying bacteria, pure water, and the gas containing oxygen to the third reaction vessel;

a delivery device for delivering a material which is a nitrification inhibitor to the second reaction vessel;

means for measuring preselected quantities of the activated sludge, the aqueous solution, the gas containing oxygen and the nitrification inhibitor to be supplied to the respective first and second reaction vessels;

means for measuring preselected quantities of the activated sludge, the pure water, and the gas containing oxygen to be supplied to the third reaction vessel;

at least one first oxygen sensor and at least one second oxygen sensor provided respectively for the first and the second reaction vessels for measuring the oxygen content either above the aqueous solution contained respectively therein or in a waste gas stream escaping respectively therefrom in use;

at least one third oxygen sensor provided for the third reaction vessel for measuring the oxygen content either above the water contained therein or in a waste gas stream escaping respectively therefrom in use; and an evaluation device which is connected to the means for measuring preselected quantities of the activated sludge, the aqueous solution and the gas containing oxygen and to the at least one first oxygen sensor and to the at least one second oxygen sensor, which is effective to determine the nitrification effectiveness of the activated sludge per unit quantity thereof, and which includes a subtraction unit for receiving output signals either directly from the at least one first oxygen sensor and from the at least one second oxygen sensor or from signals derived respectively therefrom, and for forming signals representing a difference between respective output signals of the at least one first oxygen sensor and respective output signals of the at least one second oxygen sensor wherein the evaluation device is also connected to the means for measuring preselected quantities of the activated sludge, the pure water, and the gas containing oxygen to be supplied to the third reaction vessel and to the at least one third oxygen sensor, and is effective to determine biochemical oxygen demand of the aqueous solution in the second reaction vessel by means of a subtraction unit for receiving output signals either directly from the at least one third oxygen sensor or from signals derived therefrom, and for forming signals representing a difference between respective output signals of the at least one second oxygen sensor and respective output signals of the at least one third oxygen sensor.

11. The apparatus of claim 10, wherein the first and second reaction vessels are one of (a) tubular reactors provided with a continuous flow of the materials, or (b) are each a series of agitator reactors which are connected one after another, which have an equivalent construction, and which have equivalent dimensions.

12. The apparatus of claim 10, further comprising a carbon dioxide sensor provided to at least one of the first and second reaction vessels, and wherein the evaluation device is connected to the carbon dioxide sensor, is effective to determine a carbon balance for the aqueous solution, and includes a subtraction unit for receiving output signals either directly from the carbon dioxide sensor or from signals derived therefrom, and for forming signals representing the carbon balance.

13. The apparatus of claim 10, wherein the means for measuring is one of flow volume regulators or flow volume meters.

14. The apparatus of claim 10, wherein the first and second reaction vessels communicate directly with the aqueous solution via a sampling tubule.

15. The apparatus of claim 10, wherein the first and second reaction vessels are accommodated in a thermostatically controlled environment.

16. The apparatus of claim 10, further comprising a sequence control unit connected to the evaluation device and to the means for measuring for controlling the delivery of the materials, the operation of the evaluation device, and process temperature.

17. The apparatus of claim 10, wherein the first and second reaction vessels have respective inlets and outlets, and wherein at least one of an oxygen sensor and a carbon dioxide sensor is provided at respective inlets of the first and second reaction vessels.

18. The apparatus of claim 10, wherein the at least one first oxygen sensor and the at least one second oxygen sensor are fuel cells.

* * * * *